United States Patent
Stevenson et al.

[11] Patent Number: 5,910,315
[45] Date of Patent: Jun. 8, 1999

[54] ALLOGRAFT TISSUE MATERIAL FOR FILLING SPINAL FUSION CAGES OR RELATED SURGICAL SPACES

[76] Inventors: Sharon Stevenson, 2301 Roscomare Rd., #18, Los Angeles, Calif. 90077; Arthur A. Gertzman, 45F Manchester La., West Milford, N.J. 07480

[21] Appl. No.: 08/943,549

[22] Filed: Jul. 18, 1997

[51] Int. Cl.⁶ .................................................. A61F 2/28
[52] U.S. Cl. .................... 424/422; 424/423; 424/424; 424/425; 424/426; 523/115; 523/116; 623/16; 623/17
[58] Field of Search .................... 424/422, 423, 424/424, 425, 426; 523/115, 116; 623/16, 17

[56] References Cited

U.S. PATENT DOCUMENTS

5,073,373 12/1991 O'Leary et al. .
5,236,456 8/1993 O'Leary et al. .
5,366,507 11/1994 Sottosanti .
5,593,409 1/1997 Michelson .

*Primary Examiner*—Thurman K. Page
*Assistant Examiner*—Brian K. Seidleck
*Attorney, Agent, or Firm*—Gipple & Hale; John S. Hale

[57] ABSTRACT

An extrudable allograft bone tissue material for filling surgical sites can be made from mineralized or demineralized cortical, cancellous, or cortical/cancellous bone powder. A method is disclosed for reconstituting the bone powder in a syringe which includes the steps of placing lyophilized bone material of predetermined mixed size in a syringe barrel having a distal circular opening that ranges in diameter from about 8 mm to about 15 mm and adding a volume of sterile fluid to wet the bone powders. The excess sterile fluid is drained through the bone allowing the fluid to remain in constant engagement with the bone for a period of time until the mass is fully reconstituted from its initial lyophilized state and attains self-adherence so that the mass conforms to the shape of the barrel of the syringe and retains the barrel shape and integrity after extrusion from the syringe into the surgical site in a semisolid mass.

18 Claims, 1 Drawing Sheet

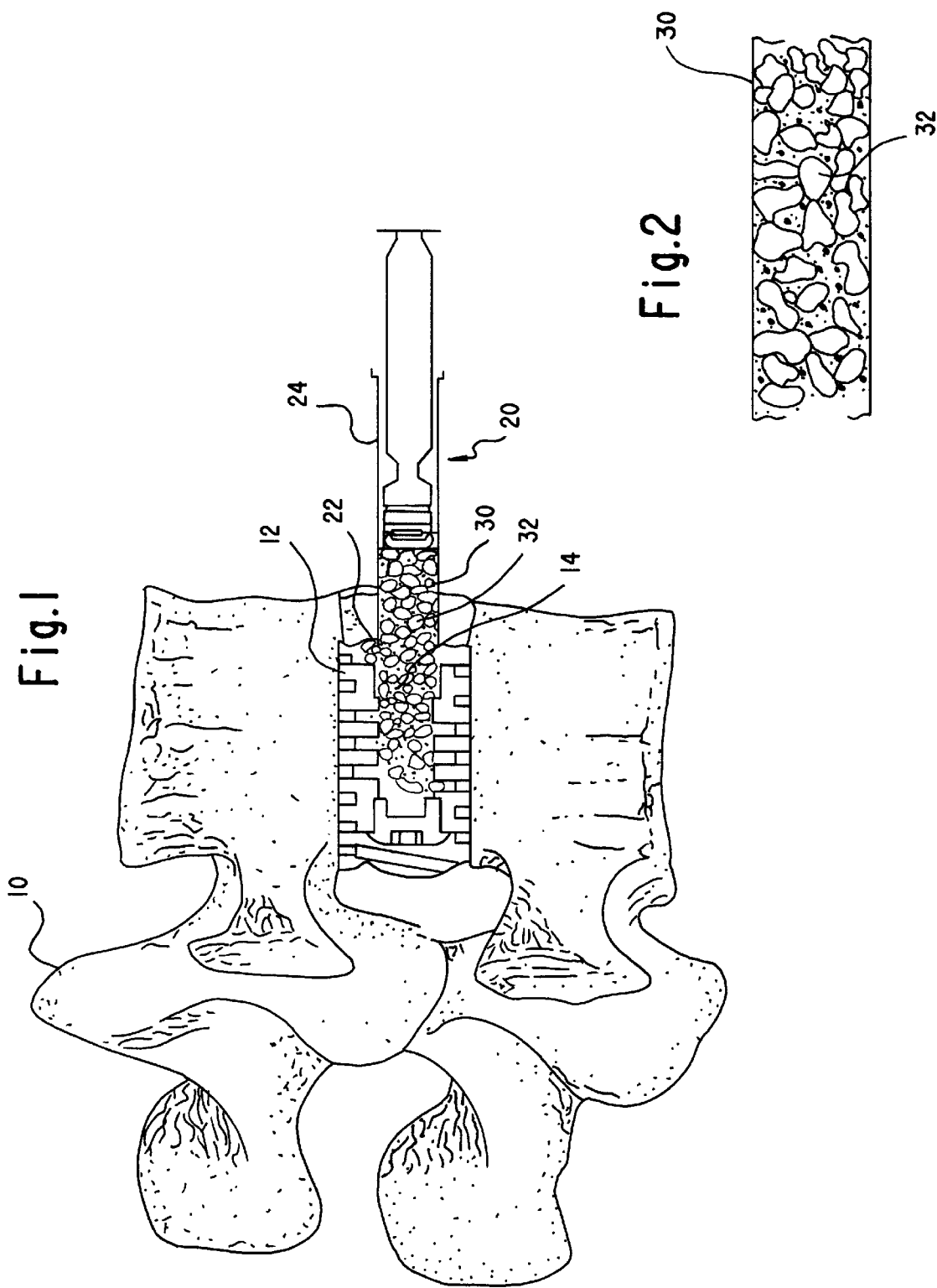

ALLOGRAFT TISSUE MATERIAL FOR FILLING SPINAL FUSION CAGES OR RELATED SURGICAL SPACES

FIELD OF THE INVENTION

The present invention generally relates to allograft bone powder compositions for use in surgery of the spinal column and more particularly to a cohesive, extrudable allograft bone powder mixture for filling surgical sites in vertebrae and other bone areas.

BACKGROUND OF THE INVENTION

Various bone tissue compositions, prosthetic devices and methods for the use thereof in spinal surgery can be found in the prior art. Bone powder has been used in the prior art to fill surgical sites during surgical procedures. For example, a collagen/demineralized bone composition material for use alone or in combination with a prosthetic device for repair of osseous tissue defects is described in U.S. Pat. No. 5,531,791 to Wolfinbarger, Jr.

Another example of bone powder in the prior art can be found in U.S. Pat. Nos. 5,073,373 and 5,484,601 to O'Leary et al. for a flowable demineralized bone powder composition for use in surgical bone repair. The carrier for the '373 demineralized bone is selected from a group consisting of glycerol, monoacetin, diacetin, and mixtures thereof and specific forms of flowable bone powder compositions include cakes, pastes, creams, and fillers. The '601 flowable demineralized bone powder composition utilizes a polyhydroxy compound and/or an ester as the carrier.

U.S. Pat. No. 5,258,043 to Stone discloses a prosthetic intervertebral disc which can be implanted in the human skeleton to act as a scaffold for regrowth of intervertebral disc material. The disc includes a dry, porous volume matrix of biocompatible and bioresorbable fibers which may be interspersed with glycosoaminoglycan molecules. The matrix is adapted to have in vivo an outer surface contour substantially the same as that of a natural intervertebral disc, whereby the matrix establishes an at least partially bioresorbable scaffold adapted for ingrowth of intervertebral fibrochondrocytes.

Conversely in U.S. Pat. No. 4,904,260 to Ray et al. two prosthetic disc capsules are implanted side-by-side into a damaged disc of the human spine to maintain both the height and the motion, including front-to-back bending, of the affected damaged discs. Each prosthetic disc capsule has a bladder enclosing a fluid containing a therapeutic material that is slowly diffusible through a semi-permeable membrane of the bladder.

A spinal implant for use in spinal stabilization is disclosed in U.S. Pat. No. 5,489,308 to Kuslich et al. The implant is described as including a hollow, cylindrical body having external threading and a plurality of openings formed radially through the body in communication with the body interior. The holes are positioned to chip bone into the implant as the implant is rotated.

Another prosthetic device for spinal repair by inserting the same into intervertebral disc spaces after the removal of an intervertebral disc or after a carpectomy is described in U.S. Pat. No. 5,514,180 to Heggeness et al. A spinal stabilization method is disclosed in U.S. Pat. No. 5,015,255 to Kuslich for fusing contiguous vertebrae in a spine and includes the step of forming an access opening into at least a layer of tissue disposed between contiguous vertebrae to be fused. Additional portions of the tissue layer as well as material of the vertebrae body portions are removed to form an enlarged chamber disposed between the contiguous vertebrae. The chamber is at least partially filled with a graft medium.

U.S. Pat. No. 4,440,750 to Glowacki et al. discloses a plastic dispersion of demineralized bone powder and reconstituted native teleopeptide collagen fibers in a continuous aqueous phase having a substantially physiologic pH and ionic strength used to repair or reconstruct bone by injecting or implanting it at the repair or construction site. The dispersion induces osteogenesis at the site.

U.S. Pat. No. 4,501,269 to Bagby discloses a process for immediate stabilization and subsequent promotion of bone-to-bone fusion in a joint where separation of the bones is restricted by surrounding ligaments or other soft tissue. A hole is bored transversely across the joint, and a cylindrical basket is driven into the hole. Stabilization of the joint is achieved by implanting a rigid cylindrical basket which is filled with the bone fragments produced during the boring step.

Another prosthetic implant is disclosed in U.S. Pat. No. 4,834,757 to Brantigan. This implant uses gauge blocks and permanent implant plugs for surgical procedures to support and fuse together adjacent vertebrae in the vertebral column. The implant plugs are rectangular with tapered front ends and tool receiving rear ends. The gauge blocks are smooth faced for removal while the implant plugs have roughened surfaces to grip the vertebrae and provide channels for bone ingrowth.

Other prior art methods of surgical repair using bone particles include methods for surgically taking bone from other anatomical sites in the patient's body to provide bone material to fill the space created surgically between the vertebral bodies. Bone tissue is frequently taken from the patient's iliac or rib, for example, for this autologous transplant procedure and placed in a spinal cage. Alternatively, the autologous bone dust created by drilling is collected and mixed with the patient's own blood to create a paste which is then placed in the cage. In another alternative procedure, animal collagen is mixed with a ceramic material or with bone and then one of these mixtures is placed inside of the cage. Yet another method encountered in the prior art comprises placing allograft bone mixed with glycerol in the cage. A commercially available product known as GRAFTON® is also used to fill the cage.

These procedures found in the prior art are clinically functional but have several features which make them undesirable for use. First of all they may involve the extra steps of collecting bone from the patient and then mixing this bone with other materials prior to surgical use inside of the patient. Secondly, these procedures may involve a higher risk of adverse reaction with the patient's tissues because of the biochemical differences between some component used in the process such as bovine collagen or glycerol which is mixed with the allograft bone particles. Thirdly, the bone chips used in the spinal cage tend to fall apart presenting problems in filling the cage as well making sure the cage is full of bone product when the cage is inserted in the vertebrae or other bone area. Glycerin or other water soluble carriers for the allograft bone are very rapidly dissolved in the body and allow the bone particles to easily separate and migrate thereby undoing the careful placement of the bone particles within the wound created during the surgery. Any attempt to introduce the dry bone chips directly into a biocompatible metal cage are generally unsuccessful because the bone chips are too small to be retained by the mesh of the cage and instead act as discrete particulate matter and consequently fall out of the cage in an uncontrolled manner. When larger chips are used, they are difficult to hold together and load into the spinal cage. The prior art also contains several bone compositions which have the consistency of a paste, a putty or a semiliquid. The present invention creates a semisolid mass capable of being extruded yet at the same time being capable of retaining the shape of the extrusion orifice.

SUMMARY OF THE INVENTION

The present invention describes a method of using freeze dried cortical, cancellous, and mixed cortical/cancellous bone particles having a specific range of particle sizes and containing the protein components of the bone and wetting the same to form a mass capable of maintaining its shape when extruded from a syringe to fill a spinal fusion cage or a bone defect site. The method of wetting the bone tissue to conform to a predetermined shape and creating conditions which allow for the retention of that shape's integrity after extrusion from the syringe is an important factor in the success of the surgical procedure.

Consequently, the bone particles including the protein components are wetted by water or saline solution in a syringe and allowed to rehydrate; this enables the bone and carrier mixture to be extruded from a cylinder while maintaining the shape of the interior of the barrel cylinder thus allowing the surgeon to completely fill the cage with bone filler material. The addition of glycerol to the solution maximizes the amount of moisture within the swollen tissue. The desired consistency of the resulting composite bony filling material is dense enough to retain its shape when extruded from the barrel of a cylindrical applicator such as a syringe, yet remains packed loosely enough to emerge without the application of significant force on the plunger of the syringe. This bone filler material is frequently used during surgical procedures involving anterior and posterior interbody spinal fusions. Titanium cages can be used to contain the filler material to hold it in close proximity to the surgical site while healing is occurring. The inventive bone filler material of the present invention can be made from mixed sized particles of cortical, cancellous or a combination cortical/cancellous bone material.

It is an object of this invention to provide the surgeon with a prosthetic or filler comprising a bony tissue composition made of bone particles and having sufficient internal cohesiveness and self-adhesion to be extrudable yet retain the shape of the container from which it is extruded.

It is another object of this invention to provide an extrudable, shape-retaining semisolid bone composition which offers the surgeon optimum space filling by providing a variety of ranges of particle sizes for use in surgery with the smaller particles filling the interstices between the larger particles It is yet another object of the present invention to provide the surgeon with an extrudable, shape-retaining bone composition which is comprised of either demineralized, mineralized allograft bone particles or a combination thereof.

Still another object of this invention is to provide the surgeon with an extrudable, shape-retaining allograft bone filler material which eliminates the use of chemical compounds which have the potential of provoking an adverse reaction in the patient.

It is also an object of the present invention to present an extrudable osseous tissue repair composition which minimizes or eliminates the higher risk of adverse reaction for the patients.

It is yet a further purpose of the present invention to disclose a composition of an allograft bone tissue which may be placed in and retained in a spinal surgical site which maintains the proper anatomical alignment in a manner superior to techniques previously used in the surgical art.

In the following description of the invention, an embodiment of the inventive allograft bone tissue composition is presented from which these and other objectives, novel features and advantages will be readily apparent.

BRIEF DESCRIPTION OF THE DRAWING

FIG. 1 is a schematic view of the inventive bone material being inserted into a spinal fusion cage after the material has obtained shape retention; and FIG. 2 is an enlarged cross sectional view of the composition of the bone material used in FIG. 1.

DETAILED DESCRIPTION OF THE INVENTION

The preferred embodiment and best mode of the invention is shown in FIG. 1. Frequently surgeons are required to place bone tissue into the space between vertebrae 10 to facilitate the fusion of these bones. The process involved requires the surgeon to immobilize the vertebrae involved and to reduce patient pain. Various technology can be used to fill the space created surgically between the vertebrae including several types of metal cages 12. These cages can be advantageously made of biocompatible metal such as titanium and are generally of sufficient strength to support the applied anatomical load of the patient. These cages are often filled with a material derived from the bony tissue of the patient, human bone donors or animals. As shown in FIG. 2, various sized bone allograft particles as for example 100–300 micron bone particles 30 are mixed with 400–1000 micron bone particles 32 are packed together to form the composite bone material 14.

When cages are used in the repair of the spinal column, it is preferable that the space within and surrounding the biocompatible cage can be easily and completely filled with a bone material 14 which retains a shape compatible with the interior diameter of the cage. The inventive allograft bone treatment method of the present invention facilitates this formation of the patients own bone tissue to fill the surgical site by both shaping the new growth through the surgical placement of a prepared bone tissue composition within the biocompatible support cage and/or the surgically created intervertebral space.

The invention is generally shown in FIG. 1 and includes a syringe 20 is filled with a lyophilized (i.e., freeze-dried) bone allograft tissue. Typically a 3 cc (8 mm diameter) or a 10 cc (13 mm diameter) syringe with a removable tip 22 leaving an open barrel 24 is used for the procedure. The allograft bone tissue used in the syringe can be cancellous, cortical, or a mixture of cortical/cancellous tissue. The bone tissue is typically demineralized or nondemineralized bone reconstituted in the operating room immediately prior to or during the surgical procedure by adding sterile water, a sterile water and 10% glycerol by volume, a saline solution or another biocompatible fluid such as Ringer's solution to the lyophilized bone particulate in the syringe. The fluid is drained through the packed bone chips or particles using a sufficient volume of the fluid to completely wet the bone tissue. The determination of whether or not the bone has been completely wetted is made by checking for the absence of air bubbles. A volume of fluid equal to three to six times the bulk of the bone volume is normally sufficient for adequate wetting to occur.

After fully wetting the bone chips with the selected fluid, the fluid is then allowed to remain in contact with the bone tissue particles until it is fully reconstituted from its initial lyophilized state. A period of time ranging from twenty to thirty minutes is usually sufficient to allow for the full hydration of the bone particles.

At the end of this time period when the bony tissue is fully hydrated, this tissue will self-adhere and will typically have sufficient geometric integrity to be expelled or extruded from the syringe by pressing the plunger of the syringe and yet still retain the cylindrical cross-sectional configuration created by contact with the syringe barrel.

This wet, bony cylinder of tissue may be injected into the metal cage implanted in the surgical site or, alternatively, may be injected directly into an intervertebral space formed by surgery. In one method of injecting the bony material into the surgical site, the end of the syringe may be removed by cutting it off to create a circular opening which is equal in size to the inside diameter of the syringe barrel. Alternatively the barrel can have a removable tip which is threaded or snapped onto the barrel for easy removal. The diameter of the inside of the syringe barrel may be chosen to be of a size equal to the inside diameter of the metal cage.

The above described general procedure can be further illustrated by reference to the following plurality of examples of the method used to make the inventive bone allograft composition. All bone samples in the following examples were freeze-dried as part of the manufacturing process prior to use in this inventive bone filler material. Cortical and cortical/cancellous samples were mineralized during the tissue preparation process. The cancellous samples were not mineralized. All tissues were processed in aseptic conditions and sealed under vacuum until they were or are used to make the bone filler material.

The following experiments were carried out with a 3 cc syringe being used as both the vessel for the rehydration of the bony tissue material with various fluids and as the extrusion apparatus for expelling the bony tissue mass. In the following example 3 cc syringes with the plungers removed were cut at the forward end leaving a nontapered cylindrical syringe body having an inner diameter of eight millimeters with the centimeter measurement gradations left on the side. The cut end of the syringe was sealed tightly with cellophane tape. These modified syringes served as the delivery devices for extruding the rehydrated bone preparations as cylindrical masses.

Samples of dry bone material were added to the syringe with a spatula, tamped to a loosely packed mass by tapping gently upon a hard surface, with the volume of the bone mass recorded in centimeters. Each bone sample was tapped gently to fill any air pockets within the syringe. Using a spatula, the particles adhering to the walls of the syringe were gently pushed down towards the sample mass. Each sample of bone material was mixed with Ultra "Resi-Analyzed" purity grade water, saline water or water with glycerol with the volume recorded. The water was added to the plunger end of the syringe and allowed to percolate through the dry tissue without any pressure added or the plunger being replaced. Residual water was allowed to drip from the cut end of the syringe prior to extrusion with no significant change to the bone material within. Each sample was prepared, hydrated and observed with the start time data recorded before beginning another sample.

Generally, the residual proteins present in the bone samples after processing and hydration resulted in the adherence of the particulate matter sufficient to extrude it in a cylindrical mass. The tissue swells as a result of the hydration and larger particle size effected packing ability and integrity of the mass. It was also determined that the delivery device (syringe) needs to be nontapering to protect the integrity of the cylindrical mass being extruded.

The following experiments utilized hydrated bone particulate mass for a titanium cage filling. However, the hydrated bone particulate mass can be used to fill any surgical site. Each bone sample was premeasured up to the one cubic centimeter mark in a three cubic centimeter (cc) syringe. Each syringe had the closed "luer lok" tip sealed tightly in place.

The biocompatible fluids that were used to hydrate the bone samples included water, normal saline solution and in some cases a 10 percent glycerol solution in water. The hydration fluid having a 3 ml volume was allowed to percolate through the particulate tissue at its own speed and then emerge at the lower end of the syringe. The tips of the syringes were replaced after the eluent reached the top of the bone mass within the syringe. At that time the syringe was placed in a standing position for approximately twenty minutes to allow the hydration to continue prior to the extrusion of the material. No sample of the hydrated bone particles was allowed to hydrate for longer than 40 minutes.

There appeared to be no significant difference in wetting agents, contrary to what would be normally expected. Generally, the use of larger amounts of hydrating fluid appears to be beneficial for the integration for the entire range of particle sizes used in the experiments, but the final swell size of the sample indicates that a loss of bony particulate matter occurred during the hydration process because of the eluate. If it is desired to prevent the loss of these very small sized particles, a fine screen could be incorporated into the hydrating/extrusion device to eliminate the loss of the bone material while still allowing the excess liquid to pass through and out of the vessel. It should be noted that other extrusion vehicles can be effectively used to hydrate the bone sample and deliver the same to the surgical site.

The results of the experiments indicate that a range of bone samples of the freeze-dried bone can be rehydrated successfully in a 3 cc (8 mm diameter) or 10 cc (13 mm diameter) syringe to achieve a state of self-adherence or cohesiveness sufficient to extrude the bone from the syringe in an intact plug form and fill an intervertebral spinal fixation cage. Indeed hydrated bone mass can be extruded with good integration from a cylinder having a diameter ranging from 8 to 15 mm. Extrusion did not successfully occur with a syringe having a diameter of 25 mm. The results indicated that the bone sample can be selected form a group consisting of mixed sizes of cancellous, cortical or transitional cortical/cancellous material.

The use of a smaller particulate powder in admixture with a larger granular tissue allowed for a greater degree of packing of the interstitial spaces and did not compromise the ability of the bone to remain intact after the hydration of the material and the extrusion of the same into the surgical site.

The addition of 10 percent glycerol to the water maximizes the amount of moisture retained within the swollen tissue after the hydration phase within the syringe is completed. This will increase the working time of the bone plug once the bone is extruded from the syringe barrel. The extended working time will enable the surgeon to place and manipulate the allograft bone within the spinal cage or other defect space without loss of plug integrity. The ability to thus maximize the amount of fluid retained in the bone mixture is advantageous in an operation room setting if the material is prepared for the procedure but the mixture is not used immediately.

The following examples illustrate the procedure for making the extrudable bone composition according to the present invention. Some of the following examples use the term "swell volume" which is used to refer to the volume of the bone particle sample after it has been fully hydrated.

EXAMPLE 1

In this example, two samples of freeze dried, demineralized cortical/cancellous granules having a 0.5 to 3.0 mm particle size were selectively hydrated with water or saline solution.

In one experiment a 0.6 cc sample of freeze-dried, demineralized cortical/cancellous granules having a particle size ranging from 0.5 to 3.0 mm was mixed in a 3 cc syringe with 3 ml of Ultra "Resi-Analyzed" purity grade water (which was the type of water used in all of the following examples). The elution speed of the water flowing through the syringe was very slow, requiring over five minutes. The swell volume was not noted. The resulting bone composition was chunky and exhibited poor integration.

In a second experiment a 0.6 cc sample of freeze-dried, demineralized cortical/cancellous granules having a particle size ranging from 0.5 to 3.0 mm was mixed in a 3 cc syringe with 3 ml of saline. The solution ran quickly through the sample. The swell volume was again not noted. The resulting bone composition exhibited fair to good integration and was very grainy.

EXAMPLE 2

In this example, three samples of freeze-dried, demineralized cortical bone powder having a 420 to 850 micron particle size were selectively hydrated with water, saline and 10% glycerol and water solution.

In one experiment, a 0.6 cc sample of freeze-dried, demineralized cortical bone particles having a particle size in the 420–850 micron range was mixed with 3 ml of water in a 3 cc syringe. The elution speed was relatively slow taking over five minutes. No swell volume was noted. The resulting extruded material exhibited good form and stayed together well.

In a second experiment, a 0.5 cc sample of the same bone material having the same particle size range of 420–850 microns was mixed with 3 ml of saline in a 3 cc syringe. The elution speed was slow and steady and lasted less than three minutes. A 0.7 cc swell volume was noted and the resulting compound showed good integration of the particles and moderate grain size. In a third experiment, a 0.5 cc sample of the same bone material having the same particle size of 420–850 microns was mixed with 3 ml of a 10% glycerol hydration solution in a 3 cc syringe. The elution speed was slow and steady and lasted less than three minutes. No swell volume was noted. The composition was still dry at extrusion and exhibited good integration.

EXAMPLE 3

In this example, three 1 cc samples of freeze-dried, cancellous bone powder having a 250–420 micron particle size were selectively hydrated with water, saline or a 10% glycerol solution.

In the first experiment, 1 cc of bone powder and 3 ml of water were mixed in a 3 cc syringe and exhibited a slow, steady elution speed lasting less than three minutes. No swell volume was observed and the extrusion yielded an excellent compound with excellent extrusion characteristics.

In the second experiment, 1 cc of bone powder and 3 ml of saline were mixed in a 3 cc syringe, resulting in very slow elution speed of over five minutes and a swell volume of 0.5 cc. The compound had excellent extrusion characteristics and a fine grain.

In the third experiment, a mixture of 1 cc of bone powder and 3 ml of the 10% glycerol solution in a 3 cc syringe showed a moderately slow elution speed and exhibited a 1.0 cc swell volume. The hydrated mixture had full integration and was finely grained.

EXAMPLE 4

This example used a 2.4 cc sample of freeze-dried, cancellous bone of the same type used in Example 3 having a 250–420 micron particle size. The Example 4 material was chosen because it showed good integration in the previous experiment. This larger 2.4 cc sample was placed in a 10 cc syringe rather than a 3 cc syringe to access the bone integration of a hydrated sample extruded from a 11 mm inside diameter opening. A 7.2 ml sample of water was combined with the bone in the syringe. The eluate ran through the bone sample quickly. The swell volume of the bone was 2.4 cc. The resulting compound was very well hydrated and puddled with no integration. This example did not work.

EXAMPLE 5

In this example, three 1 cc portions of a sample of freeze-dried, demineralized cortical/cancellous powder having a 0.5 to 2.0 mm particle size were selectively hydrated with water, saline, or a 10% glycerol solution.

In one experiment, 1 cc of the combined cortical/cancellous bone powder was mixed with 3 ml of water in a 3 cc syringe. The elution speed was very fast lasting less than 30 seconds and the resulting hydrated mixture showed some resistance but was fairly dry and showed poor integration. The swell volume was not noted.

In the second experiment, 1 cc of combined bone powder was mixed with 3 ml of saline in a 3 cc syringe. The elution speed was slow and steady and lasted less than three minutes. The swell volume of the bone was 0.5 cc and was very grainy and dry in appearance with poor to moderate integration.

In the third experiment, a 1.0 cc sample of the combined bone powder was mixed with 3 ml of the 10% glycerol solution in a 3 cc syringe. The eluate ran through the bone powder quickly. A 1.0 cc swell volume was noted. The composition was very grainy at extrusion and exhibited good integration.

EXAMPLE 6

In this example, two 1 cc samples of freeze dried, demineralized cortical powder with a 100–300 micron particle size were hydrated with water or saline as follows:

In the first experiment, 1 cc of cortical bone powder was hydrated with 3 ml of water in a 3 cc syringe. The elution speed was very slow becoming plugged and lasted over five minutes. A swell volume of 1.5 cc was recorded. The bony material that was extruded retained its form perfectly and exhibited excellent integration.

In the second experiment, 1 cc of cortical bone powder was mixed with 3 ml of saline in a 3 cc syringe. The syringe became plugged with bone powder and over five minutes was required for the eluate to run through the bone powder. A bone swell volume of 0.6 cc was obtained. The resulting compound showed good integration and small grain size.

EXAMPLE 7

In this example, three 1 cc samples of freeze-dried, demineralized cortical bone particles having a 500–1000 micron particle size were hydrated with water, saline and water having a 10% glycerol solution:

In the first experiment, 1 cc of cortical bone particles and 3 ml of water were mixed in a 3 cc syringe. The elution speed was slow but was less than three minutes. The swell volume was not noted. The resulting compound was a little grainier than the sample made with water and the 100–300 micron sample size used in Example 6, but it was well formed.

In the second experiment, 1 cc of cortical bone particles and 3 ml of saline were mixed in a 3 cc syringe and showed immediate flowing of the eluate through the sample. A 0.7 cc swell volume was observed. The resulting product showed excellent integration and a moderately grainy texture.

In the third experiment, 1 cc of cortical bone particles and 3 ml of 10% glycerol solution mixed in a 3 cc syringe exhibited slow elution speed lasting less than three minutes and a 1.4 cc swell volume. The product showed good integration and was moderate grained.

EXAMPLE 8

In this example, freeze-dried cancellous bone powder with a 500–1000 micron particle size was mixed with one of three hydrating agents, water, saline, and water having 10% glycerol as follows:

In the first experiment, 1 cc of bone powder and 3 ml of water were mixed in a 3 cc syringe and demonstrated an elution speed that was fairly rapid and required less than one minute. There was no swell volume noted. The product showed good integration and was dry and grainy.

In the second experiment, 1 cc of bone and 3 ml of saline was used in a 3 cc syringe and resulted in a bone swell volume of 1.0 cc. The elution speed was not noted. The product exhibited full integration and a fine to moderate graininess.

In the third experiment, 1 cc of bone powder and 3 ml of 10% glycerol solution were mixed in a 3 cc syringe and demonstrated an elution speed that was rapid and required less than one minute. The swell volume was 1.0 cc and the final product demonstrated good integration and a very grainy quality.

A mixed particulate bone sample was used in Example 9 in order to assess whether a mixed sample would hydrate faster, swell more or retain a tighter extrusion shape. Consequently, the sample used in Example 9 was conducted using a 0.75 cc sample of freeze-dried, demineralized cortical/cancellous bone powder with a particle size ranging from 100 to 300 microns was combined with a 0.25 cc sample of freeze-dried, demineralized cortical bone powder having a particle size ranging from 0.5 to 2.0 mm. These two types of bone particles were mixed in the syringe and a thin spatula was used to integrate the two tissue samples for a more even distribution of the particle sizes prior to hydration.

EXAMPLE 9

This example, as mentioned above, used a mixed particle size to determine whether the mixed particulate would hydrate faster, swell more or retain a tighter extrusion shape. The sample comprised 0.75 cc of the freeze-dried, demineralized cortical/cancellous granules having a particle size ranging from 0.5 to 2.0 mm as used in Example 5 and 0.25 cc of freeze-dried, demineralized cortical bone powder with 100–300 micron particle size. The two samples were thoroughly mixed and three 1 cc samples were taken and hydrated as follows:

In the first experiment, 1 cc of the mixed bone powder was combined with 3 ml of water in a 3 cc syringe. The elution speed was fairly rapid requiring less than one minute. The swell volume was not noted. The final compound showed good integration, large grain size and it could be rolled after extrusion.

In the second experiment, 1 cc of the mixed bone powder and 3 ml of the saline solution were mixed together in a 3 cc syringe. The combination showed a smooth flow of eluate taking less than three minutes and a 1.1 cc swell volume. The final product demonstrated full integration with moderate graininess.

In the third experiment, 1 cc of the mixed bone powder was combined with 3 ml of the 10% glycerol solution in a 3 cc syringe. The eluate ran through quickly, requiring less than one minute. A bone swell volume of 1.0 cc was recorded. The final composition had full integration and was dry looking and highly grainy.

EXAMPLE 10

In this example, a sample of freeze dried, demineralized cortical/cancellous granules having a 0.5 to 3.0 mm particle size were selectively hydrated with saline solution.

In this experiment a 2.0 cc sample of freeze-dried, demineralized cortical/cancellous granules having a particle size ranging from 0.5 to 3.0 mm was mixed in a 10 cc syringe with 10 ml of saline. The solution ran quickly through the sample. The swell volume was not noted. The resulting bone composition exhibited good integration and adhered well.

In the foregoing description, the invention has been described with reference to a particular preferred embodiment, although it is to be understood that specific details shown are merely illustrative, and the invention may be carried out in other ways without departing from the true spirit and scope of the following claims.

What we claim is:

1. A method for filling a surgical site with bone material, comprising the steps of:

placing a mass of lyophilized bone chips of predetermined mixed size ranging from 100 microns to 2.0 mm, said mass of chips including a packing of the interstitial spaces between the larger granular tissue particles of particulate cortical bone powder ranging from about 100 to about 300 microns and larger sized granular tissue particles in a straight-walled barrel of a syringe having a circular opening at the distal end thereof, ranging from about 8 mm to about 15 mm in diameter;

tamping the mass of bone chips to fill air pockets in the syringe;

adding a volume of sterile fluid ranging from about 3 to about 6 times the bulk of the volume of the mass of bone chips to provide adequate wetting;

allowing the fluid to flow through said mass of bone chip to filly hydrate the bone chips for a period of time hydrating the bone chips until the mass is fully reconstituted from its initial lyophilized state and obtains chip self-adherence conforming to the shape of the lumen of the barrel of the syringe and retain such shape and geometric integrity;

draining sterile fluid from the syringe; and depressing a plunger of the syringe and extruding the shaped bone material in a semi-solid mass which retains its shape and integrity in a surgical site.

2. A method of filling a surgical site with bone material as claimed in claim 1 wherein said sterile fluid comprises sterile water with about 10% glycerol by volume and said period of time for hydration ranges from about twenty minutes to about thirty minutes.

3. A method of filling a surgical site as claimed in claim 1 wherein said surgical site is a spinal fusion cage.

4. A method of filling a surgical site with a shape-retaining, semi-solid bone composition, comprising the steps of:

placing a plurality of lyophilized bone particles of mixed sizes ranging from a particulate powder mixed with larger granular tissue particles, said lyophilized bone particles comprising a mixture containing about 75% by volume of lyophilized, demineralized cortical/cancellous bone powder ranging from 0.5 to 2 mm particle size and about 25% by volume of lyophilized, demineralized cortical bone powder ranging from 100 to 300 micron particle size to provide a bone composition with a packing of the interstitial spaces between the larger granular tissue particle with particulate powder or other granular tissue particles in a straight-walled extrusion vessel having an opening at the distal end thereof which opening has substantially the same dimensions as the interior of a spinal fusion chamber;

pouring a volume of hydrating solution into an open proximal end of said extrusion vessel and allowing the solution to flow through said mass of bone particles to fully hydrate same;

removing the air bubbles from the hydrating solution which adhere to said plurality of bone particles;

allowing the bone particles to hydrate for at least 20 minutes in said solution so that said bone particles become an extrudable, shape-retaining semi-solid mass; and extruding said bone particle composition from said extrusion vessel into said surgical site in a semi-solid shape which substantially retains the shape of the interior of said extrusion vessel.

5. A method of filling a surgical site with a shape-retaining, semi-solid bone composition as claimed in claim 1 wherein said bone particles are comprised of cancellous bone powder having a particle size ranging from about 250 to about 420 microns.

6. A method of filling a surgical site with a shape-retaining, semi-solid bone composition as claimed in claim 1 wherein said demineralized cortical bone particles packing the interstitial spaces have a particle size ranging from about 420 to about 850 microns.

7. A method of filling a surgical site with a shape-retaining, semi-solid bone composition as claimed in claim 4 wherein said hydrating solution is saline.

8. A method of filling a surgical site with a shape-retaining, semi-solid bone composition as claimed in claim 4 wherein said hydrating solution is at least 90% water by volume and not more than 10% glycerol by volume.

9. A method of filling a surgical site with a shape retaining semi-solid bone composition as claimed in claim 4 wherein said hydrating solution volume is about three times the bulk volume of the bone composition.

10. An extrudable, shape-retaining bone filler composition, comprising:

a mass of freeze dried demineralized bone particles having a particle size ranging from about 100 to about 1,000 microns; and packed together with the smaller particles packing the interstitial spaces between the larger granular tissue particles in a walled container so that the interstices formed between the largest bone particles are substantially filled; and, a sterile hydrating agent having a volume ranging from one to three to one to six in relation to the volume of the bone particle mass, and an elution speed through the bone particle mass ranging from two to six minutes, said bone particle mass being placed in contact with said hydrating agent for at least twenty minutes to provide a swell volume of the bone particles of at least about 40%.

11. An extrudable, shape-retaining bone filler composition as claimed in claim 10 wherein said hydrating agent is water.

12. An extrudable, shape-retaining bone filler composition as claimed in claim 10 wherein said hydrating agent is a saline solution.

13. An extudable, shape-retaining bone filler composition as claimed in claim 10 wherein said hydrating agent is at least 90% water by volume and not more than 10% glycerol by volume.

14. An extrudable, shape-retaining bone filler composition, comprising:

a mass of freeze dried demineralized cancellous bone particles having a particle size ranging from about 250 to 420 microns; packed together in a walled container so that the interstices between the largest bone particles are substantially filled; and, a sterile hydrating agent having a volume ranging from one to three to one to six in relation to the volume of the bone particle mass, and an elution speed over five minutes and when immersing the bone particle mass, for at least twenty minutes provides a swell volume of the bone particles ranging from about 50% to 150%.

15. An extrudable shape retaining bone filler composition as claimed in claim 14 wherein said hydrating agent is water.

16. An extrudable, shape-retaining bone filler composition as claimed in claim 14 wherein said hydrating agent is at least 90% water by volume and not more than 10% glycerol by volume.

17. An extrudable, shape-retaining bone filler composition as claimed in claim 10 wherein said bone particles are cortical bone particles ranging in particle size from about 500 to about 1,000 microns.

18. An extrudable, shape-retaining bone filler composition as claimed in claim 10 wherein said bone particles are cortical bone particles ranging in particle size from about 420 to about 850 microns.

* * * * *